US009526489B2

(12) United States Patent
Burkhart

(10) Patent No.: US 9,526,489 B2
(45) Date of Patent: Dec. 27, 2016

(54) LOAD-SHARING RIP-STOP DOUBLE ROW REPAIRS

(71) Applicant: Arthrex, Inc., Naples, FL (US)

(72) Inventor: Stephen S. Burkhart, San Antonio, TX (US)

(73) Assignee: Arthrex, Inc., Naples, FL (US)

( * ) Notice: Subject to any disclaimer, the term of this patent is extended or adjusted under 35 U.S.C. 154(b) by 853 days.

(21) Appl. No.: 13/872,711

(22) Filed: Apr. 29, 2013

(65) Prior Publication Data

US 2013/0296936 A1 Nov. 7, 2013

Related U.S. Application Data

(60) Provisional application No. 61/641,369, filed on May 2, 2012.

(51) Int. Cl.
*A61B 17/04* (2006.01)
*A61B 17/06* (2006.01)

(52) U.S. Cl.
CPC ..... *A61B 17/0401* (2013.01); *A61B 17/06166* (2013.01); *A61B 90/92* (2016.02); *A61B 2017/044* (2013.01); *A61B 2017/0414* (2013.01)

(58) Field of Classification Search
CPC .............. A61B 90/92; A61B 2017/044; A61B 17/0401; A61B 17/06166
See application file for complete search history.

(56) References Cited

U.S. PATENT DOCUMENTS

2007/0191849 A1* 8/2007 ElAttrache ......... A61B 17/0401
606/326

* cited by examiner

*Primary Examiner* — Thomas McEvoy
(74) *Attorney, Agent, or Firm* — Blank Rome LLP

(57) ABSTRACT

A load sharing rip-stop construct and technique for soft tissue repair, particularly rotator cuff repair. A suture tape is inserted through the soft tissue (rotator cuff) at a first location. At least one suture anchor is inserted into bone, adjacent the soft tissue, the anchor being loaded with at least one length of an suture with two ends. The ends of the suture are passed through the soft tissue at a second location which is medial to the first location, and secured in bone at the second location with an anchor. The suture tape is then passed over the soft tissue and secured into the bone at a third location which is lateral to the first and second locations. The suture tape acts as a "rip-stop," not only providing resistance to tissue cutout for the suture, but also enhancing load distribution.

11 Claims, 3 Drawing Sheets

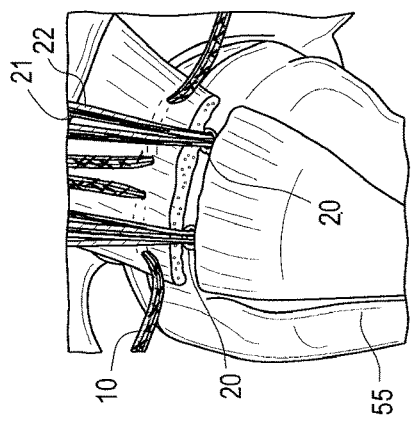
FIG. 2A
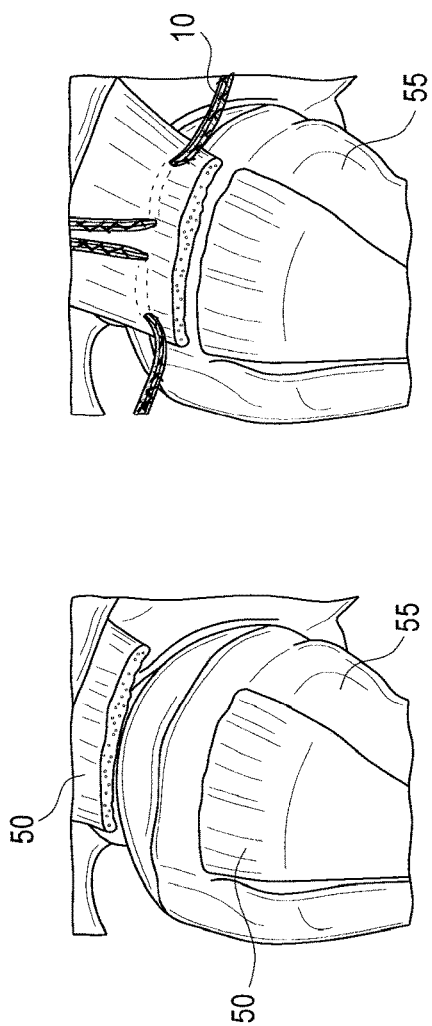
FIG. 2B
FIG. 2C
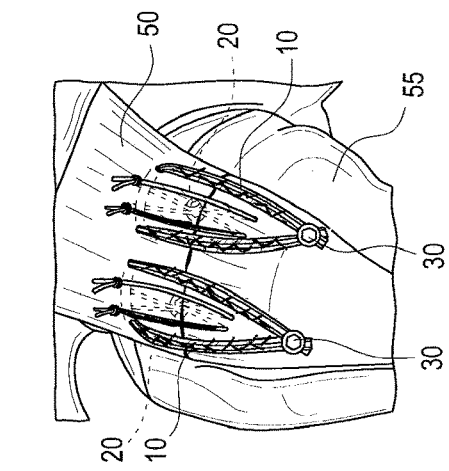
FIG. 2D
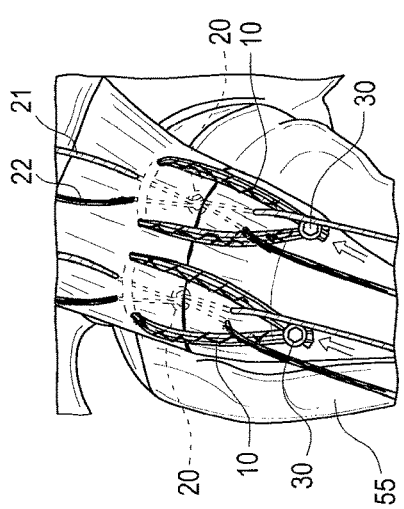
FIG. 2E
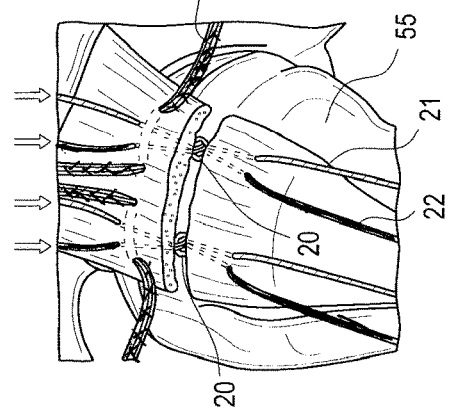
FIG. 2F

LOAD-SHARING RIP-STOP DOUBLE ROW REPAIRS

CROSS-REFERENCE TO RELATED APPLICATIONS

This application claims the benefit of U.S. Provisional Application No. 61/641,369 filed May 2, 2012, the disclosure of which is incorporated by reference in its entirety herein.

FIELD OF THE INVENTION

The present invention relates to arthroscopic surgery and, more specifically, to improved methods of attaching tissue to bone, such as rotator cuff repair.

BACKGROUND OF THE INVENTION

Reattachment techniques of soft tissue to bone employing knotless fixation devices are known in the art, particularly for the formation of single and double row constructs in arthroscopic rotator cuff repairs. For example, the Speed-Fix™ and SpeedBridge™ techniques, both developed by Arthrex, Inc., use a threaded swivel anchor (such as Arthrex SwiveLock® C anchor as disclosed and described in U.S. Patent Application Publication No. 2007/0191849) combined with FiberTape® (disclosed in U.S. Pat. No. 7,892,256) to create a quick and secure SpeedFix™ construct (a knotless single row repair) or a SpeedBridge™ construct (a knotless double row repair) with no knots and very few suture passing steps.

In the SpeedBridge™ technique, a swivel anchor (preferably an Arthrex 4.75 mm SwiveLock® C anchor) loaded with one strand of FiberTape® is inserted into a medial bone socket. A FiberLink™ and Scorpion™ shuttle both Fiber-Tape® tails through the rotator cuff simultaneously. Next, one FiberTape® tail from each medial anchor is retrieved and loaded through another SwiveLock® C eyelet. The loaded eyelet is inserted into a prepared lateral bone socket until the anchor body contacts bone, and the tension is adjusted if necessary. The SwiveLock® C driver is rotated in a clockwise direction to complete the insertion. Using an open ended FiberWire® cutter, the FiberTape® tails are cut to complete the technique.

The above-described SpeedFix™ and SpeedBridge™ suture bridge techniques restore the anatomic footprint and are particularly suitable for rotator cuff tears which usually occur at the tendon-bone insertion. However, at times, a tear can occur more medially or be accompanied by lateral tendon loss, precluding the ability to perform a double row repair. "Rip-stop" suture configurations have been shown to improve load to failure compared with simple or mattress stitch patterns. C. B. Ma et al., "Biomechanical evaluation of arthroscopic rotator cuff stitches," *J Bone Joint Surg Am,* Vol. 86, pp. 1211-1216 (2004). As described in the Ma publication, a rip-stop suture may be placed as an isolated suture or with the use of a double- or triple-loaded anchor. In the case of an anchor, the first set of anchor sutures are used to create a mattress stitch and the remaining sutures are passed medial to lateral in a simple pattern. A rip-stop suture with a double-loaded anchor has a load to failure equivalent to a modified Mason-Allen stitch. In a follow-up study, it was reported that a triple-loaded anchor with a horizontal rip-stop stitch and two simple stitches demonstrate even less elongation with cyclic loading (i.e., maintained loop security) and a higher ultimate load to failure compared to the rip-stop configuration with a double-loaded anchor. M. Baleani et al., "Comparative study of different tendon grasping techniques for arthroscopic repair of the rotator cuff," *Clin Biomech (Bristol, Avon),* Vol. 21, pp. 799-803 (October 2006). Notably, the highest load to failure is achieved with a classic double-row repair.

Accordingly, a new surgical technique for double row constructs with a reinforced medial row (especially for rotator cuff repairs with lateral tendon loss), using a "rip-stop" suture pattern, is needed.

SUMMARY OF THE INVENTION

The present invention provides methods and constructs for reinforced double row rotator cuff repairs using a knotless load-sharing rip-stop suture in the form of a high strength suture tape. The methods of the present invention provide enhanced management of poor soft tissue and bone quality in arthroscopic repairs (for example, arthroscopic rotator cuff repairs).

A method of soft tissue repair according to the present invention comprises inter alia the steps of: (i) inserting a suture or a suture tape through soft tissue at a first location so that the suture or suture tape extends about parallel to a musculotendinous junction; (ii) inserting one or more suture anchors into bone and adjacent the soft tissue, the one or more suture anchors comprising at least one flexible strand with two ends; (iii) passing at least one end of the flexible strand through the soft tissue at a second location which is medial to the first location of the suture or suture tape; and (iv) passing at least one end of the suture or suture tape over the soft tissue and securing the at least one end into the bone at a third location which is lateral to the first and second locations.

A method of soft tissue repair according to the present invention comprises inter alia the steps of: (i) inserting a suture or a suture tape through soft tissue at two different first locations so that the suture or suture tape extends about parallel to a musculotendinous junction; (ii) inserting at least one anchor (for example, first and second anchors) into bone and adjacent the soft tissue, at two different second locations, each of the first and second anchors comprising two flexible strands and four ends; (iii) passing two of the four ends of the flexible strands of each of the first and second anchors through the soft tissue at two different third locations which are medial to the two different first locations of the suture tape; and (iv) passing each limb of the suture or suture tape over the soft tissue and securing each limb of the suture or suture tape into the bone at two different fourth locations which are lateral to the first, second and third locations.

The technique of the present invention is particularly useful for rotator cuff repair, and addresses medial tendon tears or tears with lateral tendon loss which may be precluded by standard techniques. As noted above, rip-stop suture configurations have been shown to improve load to failure compared with simple or mattress stitch patterns and may be particularly valuable in these settings. The constructs of the present invention provide a rip-stop rotator cuff repair that combines the advantages of a rip-stop suture (by providing resistance to tissue cutout) and a double row of load-sharing suture anchors (minimizing the load per anchor and therefore the load per suture within each anchor).

Unlike the prior art techniques in which the mattress stitch and simple stitch are based off the same anchor, in the techniques described below, the rip-stop suture is independently secured so that it not only provides resistance to tissue cutout for the simple sutures but also enhances load distribution.

These and other features and advantages of the present invention will become apparent from the following description of the invention that is provided in connection with the accompanying drawings and illustrated embodiments of the invention.

BRIEF DESCRIPTION OF THE DRAWINGS

FIGS. 2A-2F illustrate schematic views of a dual rip-stop rotator cuff repair.

DETAILED DESCRIPTION OF THE INVENTION

Figure 1C:
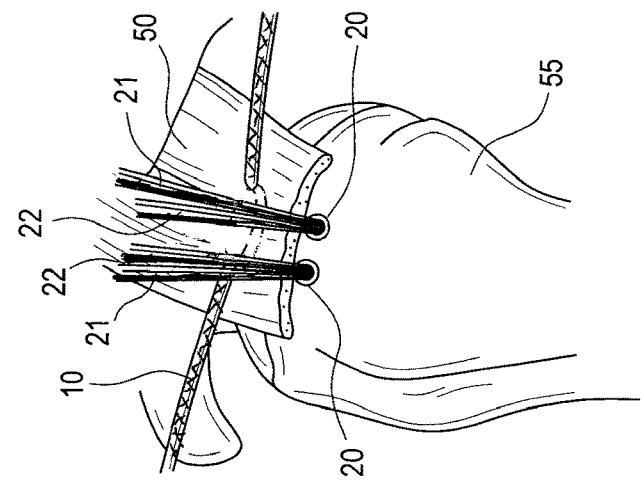
FIGS. 1A-1F illustrate schematic views of an anchor-based rip-stop rotator cuff repair for a rotator cuff tear with lateral tendon loss (left shoulder, lateral-to-medial view)

The present invention provides methods of forming knotless single and multiple row constructs with a high strength rip-stop suture, such as FiberTape®.

Steps of an exemplary rotator cuff repair with load-sharing rip-stop suture tape in accordance with the present invention includes the following steps:

1. A suture tape rip-stop is placed as a free inverted mattress stitch in the rotator cuff about 3 mm lateral to the musculotendinous junction;
2. Medial anchors are placed in the greater tuberosity;
3. Sutures from the anchors are placed as simple stitches that pass medial to the rip-stop suture;
4. The suture tape rip-stop is retrieved to encircle the rotator cuff sutures;
   a. The anterior limb of the rip-stop is retrieved anterior to the rotator cuff suture limbs;
   b. The posterior limb of the rip-stop is retrieved posterior to the rotator cuff suture limbs;
5. The anterior and posterior limbs of the suture tape are secured to lateral anchor(s); and
6. The rotator cuff sutures are tied, which pass medial to the rip-stop.

Although the specific embodiments detailed below will be described with reference to specific repairs using a suture tape such as FiberTape® suture and knotless fixation devices such as SwiveLock® anchors, the invention is not limited by this exemplary- embodiment. Accordingly, the present invention contemplates tissue repairs wherein flexible strands with different width and/or diameters (for example, tapes and/or braids and/or suture tapes or combinations of tapes and sutures) are employed and with any fixation devices such as anchors, i.e., not limited to knotless fixation devices such as SwiveLock® anchors. Further, although the embodiments below will be described with reference to particular rotator cuff repairs, the invention contemplates repairs of any soft tissue, ligament, tendon, etc. For example, the invention contemplates ant repair/reinforcement of soft tissue, such as rotator cuff repair, Achilles tendon repair, patellar tendon repair, ACL/PCL reconstruction, hip and shoulder reconstruction procedures, among many others. Although single and double-row repairs are detailed below (with one or two exemplary FiberTape® sutures passed through soft tissue), the invention also contemplates repairs with any numbers of multiple rows and/or with any number of flexible strands (i.e., with multiple suture tapes and/or wide sutures) as required by the specific and extent of each repair.

The load-sharing rip-stop double row construct (for tissue repairs such as rotator cuff repair) of the present invention, described in more detail below, combines the advantages of a wide rip-stop suture tape and a double-row repair (FIGS. 1 and 2). The technique is particularly useful for cases involving medial tears in which there is limited medial tendon that precludes a standard double-row repair. As detailed below, one or two FiberTape® rip-stop sutures are secured to two BioComposite SwiveLock® anchors laterally in a modified SpeedFix™ repair. The FiberTape® rip-stop provides resistance to tissue cut out for simple sutures that are passed from a medial row of two BioComposite Corkscrew® FT anchors.

A rip-stop suture is an effective method of avoiding cinching while improving resistance to suture cutout. An anterior-to-posterior mattress stitch formed of wider suture such as suture tape (placed independently or originating from an anchor) can be placed through the rotator cuff and tied on itself. Subsequently, simple sutures from an anchor are passed medial to the rip-stop suture, which distributes the medial-to-lateral tensile forces and effectively decreases the chance of suture cutout. Such a rip-stop suture may be placed as an isolated suture or with the use of a double- or triple-loaded anchor (or multiple-loaded anchors). In the case of an anchor, the first set of anchor sutures is used to create a mattress stitch and the remaining sutures are passed medial to lateral in a simple pattern.

An integral feature of the present invention is that the FiberTape® rip-stop suture is load-sharing and thereby takes some of the stress off the fixation sutures of the other anchors. In prior applications of rip-stop sutures, the rip-stop sutures have not been load-sharing and, therefore, have been less protective of poor-quality tissues than the rip-stop sutures of the present invention.

The present invention provides a unique approach for challenging rotator cuff repairs that include either poor tendon quality or a short medial tendon stump using exemplary FiberTape® suture tapes and SwiveLock® anchors for reinforcement. FiberTape® is #2 FiberWire® with a 2 mm wide overbraid that has been shown to have 30% higher resistance to pulling through tendon than standard #2 suture and can be used to augment a single row repair using fixation devices such as Corkscrew® FT suture anchors. One or two FiberTape® sutures are used to create the rip-stop. The FiberTape® sutures are secured laterally with knotless SwiveLock® anchors in a modified SpeedFix™ repair that not only reinforces the medial stitches, but also shares the load carried by the simple sutures.

Two preferred embodiments of the technique of the present invention (single and dual rip-stop) are now described with reference to the drawings.

FIGS. 1A-1F illustrate schematic views of an anchor-based rip-stop rotator cuff repair for a rotator cuff tear with lateral tendon loss (left shoulder, lateral-to-medial view).

Figure 1B:
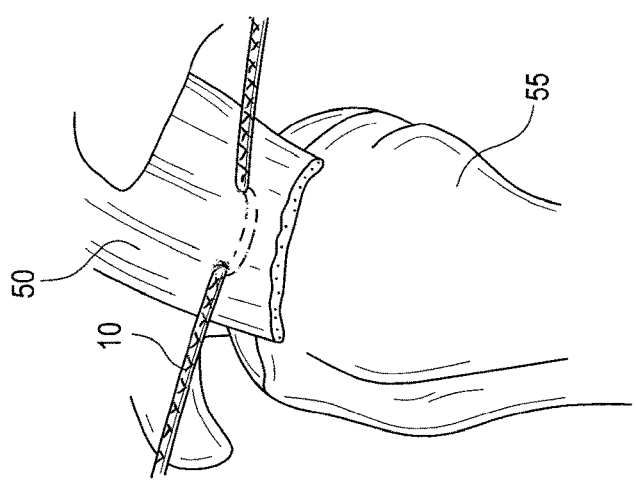
Figure 1A:
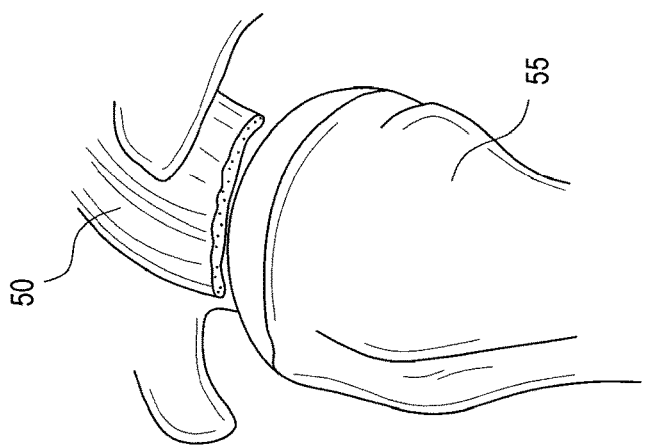

FIG. 1A: In this rotator cuff tear with lateral tendon loss, there is limited space to achieve fixation in the remaining medial tendon 50 (rotator cuff 50).

FIG. 1B: A suture tape (FiberTape® suture) rip-stop 10 has been placed as an inverted mattress stitch in the rotator cuff 50.

FIG. 1C: Two medial anchors 20 (for example, BioComposite Corkscrew® anchors 20) are placed approximately 5 mm lateral to the articular margin.

Figure 1D:
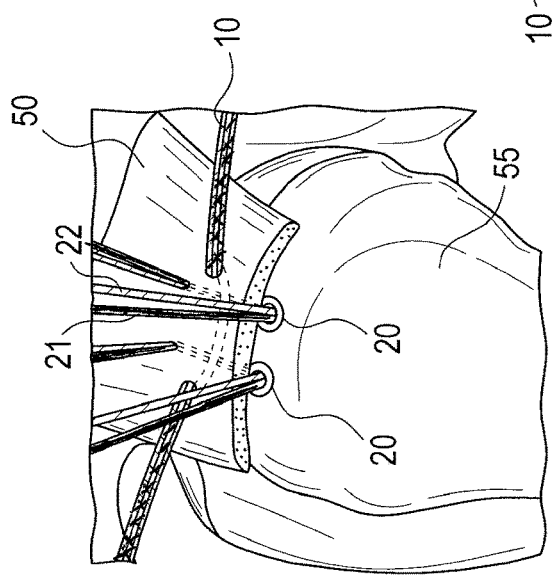

FIG. 1D: The sutures 21, 22 from these anchors 20 are passed medial to the suture tape rip-stop stitch 10 (arrows).

Figure 1E:
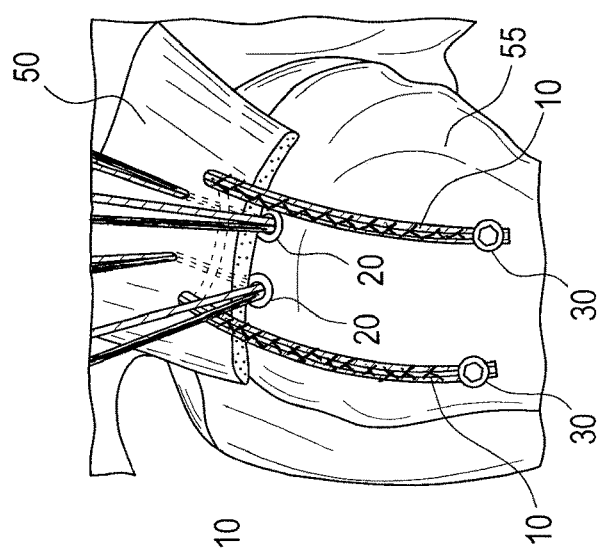

FIG. 1E: Before sutures 21, 22 from the medial anchors 20 are tied, the suture tape rip-stop stitch 10 is secured to bone 55 with two lateral knotless anchors 30 (BioComposite SwiveLock® C anchors 30).

Figure 1F:
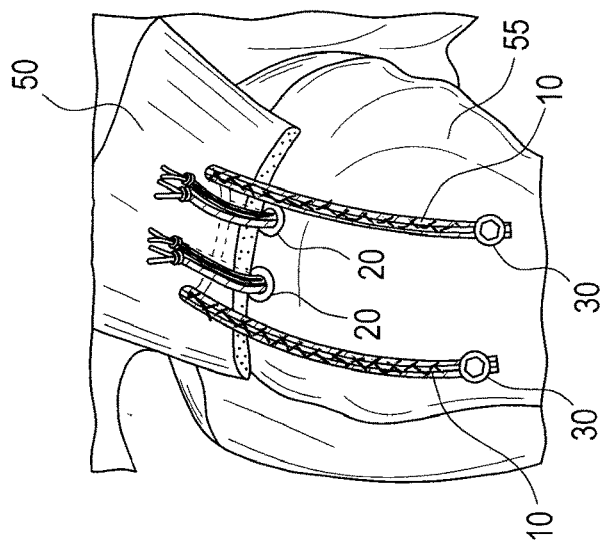

FIG. 1F: The suture limbs 21, 22 from the medial anchors 20 are tied to complete the repair.

FIGS. 2E-2F are schematic illustrations of a dual rip-stop rotator cuff repair.

FIG. 2A: In this medial rotator cuff tear with rotator cuff 50 provided with a lateral tendon stump, there is limited space to achieve fixation in the medial tendon.

FIG. 2B: Two FiberTape® rip-stop sutures 10 are placed about 3 mm lateral to the musculotendinous junction as inverted mattress stitches.

FIG. 2C: Two medial anchors 20 (for example, BioComposite Corkscrew® FT anchors 20) are placed in bone 55 (the greater tuberosity bone bed).

FIG. 2D: Suture limbs 21, 22 from the medial anchors 20 (BioComposite Corkscrew® anchors 20) are passed medial to the rip-stop stitches. In addition, the opposite suture limbs 21, 22 are passed through the lateral tendon stump.

FIG. 2E: The FiberTape® rip-stop sutures 10 are secured laterally with two knotless anchors 30 (for example, BioComposite SwiveLock® C anchors 30). An exemplary SwiveLock® C anchor is disclosed and described in U.S. Patent Application Publication No. 2007/0191849, the disclosure of which is incorporated in its entirety herewith. These rip-stop sutures are load sharing and are secured before the Corkscrew anchor sutures 21, 22 are tied. During this step, it is important to retrieve the rip-stop sutures so that they surround the lateral sutures limbs from the Corkscrew® anchors 20.

FIG. 2F: The repair is completed by tying the sutures limbs 21, 22 from the Corkscrew anchors 20.

The flexible strands/tapes 10, 21, 22 of the present invention may contain a high strength suture material with surgically-useful qualities, including knot tie down characteristics and handling, such as Arthrex FiberWire® FiberWire suture disclosed in U.S. Pat. No. 6,716,234, the disclosure of which is incorporated herein by reference. The sutures/tapes may be provided with optional colored strands to assist surgeons in distinguishing between suture lengths with the trace and suture lengths without the trace.

The flexible strands/tapes 10, 21, 22 of the present invention may be also provided in the form of a suture tape (such as the FiberTape® disclosed in U.S. Pat. No. 7,892,256, the disclosure of which is herein incorporated by reference in its entirety), or a combination of suture and suture tape.

Preferably, the strands/tapes 10, 21, 22 may be provided as color contrasting strands to assist surgeons in distinguishing between them while they are loaded through the eyelet of a suture anchor or passed through tissue, for example. At least one of the limbs may be visually coded, making identification and handling of the suture legs simpler. Multiple strands/tapes 10, 21, 22 may be employed with the techniques of the present invention.

The single and multiple row constructs of the present invention may be employed in surgical procedures for repair/reinforcement of soft tissue, such as rotator cuff repair, Achilles tendon repair, patellar tendon repair, ACL/PCL reconstruction, hip and shoulder reconstruction procedures, among many others. The single and double row constructs may be employed with additional implant material(s) such as grafts or patches provided arthroscopically (preferably under the tissue or above the tissue) prior to implanting the lateral rows of the repair system. The graft or patch may be allograft or porous collagen material, and may be optionally hydrated with bone marrow aspirate. The graft or patch may be placed either above or below the soft tissue (for example, the rotator cuff) and secured into position at the repair site.

The rip-stop rotator cuff repair techniques described above combine the advantages of a rip-stop suture (by providing resistance to tissue cutout) and a double-row repair (by increasing load-sharing properties). In addition, the techniques use a suture tape that has shown improved biomechanical properties compared with standard high-strength sutures. The techniques are particularly useful for cases in which there is limited medial tendon that precludes a suture-bridging double-row repair.

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all fall within the scope of the invention. Accordingly, the invention is not to be considered as limited by the foregoing description.

What is claimed is:

1. A method of soft tissue repair, comprising the steps of: inserting a suture tape having two limbs through soft tissue at two different first locations so that the suture tape extends about parallel to a musculotendinous junction; inserting first and second anchors into bone and adjacent the soft tissue, at two different second locations, each of the first and second anchors being loaded with two flexible strands having four ends; passing two of the four ends of the flexible strands of each of the first and second anchors through the soft tissue at two different third locations which are medial to the two different first locations of the suture tape; and passing each limb of the suture tape over the soft tissue and securing each limb of the suture tape into the bone at two different fourth locations which are lateral to the first, second and third locations.

2. The method of claim 1, further comprising the step of securing the four ends of the flexible strands of each of the first and second anchors over the soft tissue by tying four static knots over the soft tissue.

3. The method of claim 1, wherein at least one of the flexible strands is suture.

4. The method of claim 3, wherein the suture is formed of ultrahigh molecular weight polyethylene.

5. The method of claim 1, wherein the flexible strand has a width greater than that of the elongated flexible member.

6. The method of claim 1, wherein the flexible strand is a suture tape or a combination of suture and suture tape.

7. The method of claim 1, wherein the flexible strand has a width greater than that of the elongated flexible member.

8. The method of claim 1, further comprising the step of securing each limb of the suture tape into the bone with a knotless fixation device.

9. The method of claim 8, wherein the knotless fixation device is a push-in type anchor, a screw-in anchor or a swivel anchor.

10. The method of claim 8, wherein knotless fixation device is a swivel anchor.

11. The method of claim 8, wherein the knotless fixation device comprises an anchor body and an anchor tip, and wherein the anchor body is configured to be inserted over the anchor tip for securing the anchor body and the flexible strand into the bone.

\* \* \* \* \*